US012797551B2

(12) United States Patent
Garrec et al.

(10) Patent No.: US 12,797,551 B2
(45) Date of Patent: Nov. 17, 2026

(54) MEDICAL CONTAINER AND A DRUG DELIVERY DEVICE COMPRISING SAID MEDICAL CONTAINER

(71) Applicant: Becton Dickinson France, Le Pont de Claix (FR)

(72) Inventors: Ronan Garrec, Claix (FR); Patrick Robert, Seyssins (FR); Olivier David, Saint-Michel-les-Portes (FR); Christian Pauly, Saint-Martin D'Uriage (FR)

(73) Assignee: Becton Dickinson France, Le Pont-de-Claix (FR)

( * ) Notice: Subject to any disclaimer, the term of this patent is extended or adjusted under 35 U.S.C. 154(b) by 1083 days.

(21) Appl. No.: 17/622,409

(22) PCT Filed: Jun. 25, 2020

(86) PCT No.: PCT/EP2020/067908
§ 371 (c)(1),
(2) Date: Dec. 23, 2021

(87) PCT Pub. No.: WO2020/260503
PCT Pub. Date: Dec. 30, 2020

(65) Prior Publication Data

US 2022/0355036 A1 Nov. 10, 2022

(30) Foreign Application Priority Data

Jun. 28, 2019 (EP) .................................... 19305877

(51) Int. Cl.
*A61M 5/31* (2006.01)
*A61M 5/34* (2006.01)

(52) U.S. Cl.
CPC .......... *A61M 5/3134* (2013.01); *A61M 5/345* (2013.01)

(58) Field of Classification Search
CPC ........ A61M 5/344; A61M 5/347; A61M 5/34; A61M 5/3129; A61M 5/3134; A61M 5/3293; A61M 5/345; A61M 5/32; A61M 5/31; A61M 5/178; A61M 5/28; A61M 2005/3104; A61M 2005/3106;
(Continued)

(56) References Cited

U.S. PATENT DOCUMENTS 6,196,998 B1 * 3/2001 Jansen ............... A61M 5/3134 604/111
2006/0106349 A1 5/2006 Kito et al.
(Continued)

FOREIGN PATENT DOCUMENTS

EP 2445556 B1 5/2019
JP 2005319118 A 11/2005
(Continued)

*Primary Examiner* — Kevin C Sirmons
*Assistant Examiner* — Alexandra Lalonde
(74) *Attorney, Agent, or Firm* — The Webb Law Firm

(57) ABSTRACT

A medical container includes a tubular barrel defining a reservoir for a medical product and a longitudinal distal tip defining a fluid path in communication with the reservoir in order to allow the medical product to be expelled from the medical container, the distal tip and the barrel are made of glass and the distal tip is provided with a thread, the thread able to connect the distal tip to a connecting element having a complementarily shaped internal thread.

22 Claims, 1 Drawing Sheet

(58) Field of Classification Search
CPC .. A61M 2039/1033; A61M 2039/1038; A61M 2039/1077; A61M 2039/1094; A61M 39/10
See application file for complete search history.

(56) References Cited

U.S. PATENT DOCUMENTS

| | | | | |
|---|---|---|---|---|
| 2008/0033347 | A1* | 2/2008 | D'Arrigo .............. | A61M 5/347<br>604/93.01 |
| 2011/0130717 | A1 | 6/2011 | David et al. | |
| 2012/0130351 | A1 | 5/2012 | Alvain | |
| 2012/0179108 | A1 | 7/2012 | Delabie | |
| 2014/0339812 | A1* | 11/2014 | Carney ................. | A61J 1/2096<br>29/525.02 |
| 2016/0206821 | A1 | 7/2016 | Horiuchi et al. | |
| 2017/0014616 | A1* | 1/2017 | Davis .................... | A61M 39/10 |
| 2018/0161524 | A1 | 6/2018 | Flippe et al. | |

FOREIGN PATENT DOCUMENTS

| | | | |
|---|---|---|---|
| WO | 2011125475 | A1 | 10/2011 |
| WO | 2016198580 | A1 | 12/2016 |

* cited by examiner

MEDICAL CONTAINER AND A DRUG DELIVERY DEVICE COMPRISING SAID MEDICAL CONTAINER

CROSS-REFERENCE TO RELATED APPLICATIONS

This application is the United States national phase of International Application No. PCT/EP2020/067908 filed Jun. 25, 2020, and claims priority to European Patent Application No. 19305877.3 filed Jun. 28, 2019, the disclosures of which are hereby incorporated by reference in their entirety.

BACKGROUND OF THE DISCLOSURE

The present disclosure relates to a medical container and to a drug delivery device comprising said medical container.

DESCRIPTION OF RELATED ART

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a medical container or a drug delivery device of the disclosure, and the "proximal direction" is to be understood as meaning the opposite direction to said direction of injection, that is to say the direction towards the user's hand holding a medical container or a drug delivery device of the disclosure as for an injection operation.

Basically, drug delivery devices, such as for example syringes, are preferably made of glass for its high chemical passivity, its low gas permeability and high transparency, which allows an extended storage and an easy inspection.

The drug delivery devices usually comprise a container forming a reservoir for containing a medical product. The container has a distal end in the form of a longitudinal tip defining an axial passageway through which the medical product is expelled from the container. However, this longitudinal tip does not allow parenteral administration by itself and must either comprise a staked needle or an adaptor allowing the connection of the syringe to a connector such as a needle hub or an intravenous (IV) line.

It is important that the connection between the drug delivery device and the adaptor is strong enough to prevent accidental disengagement, either during connection of the connector onto the drug delivery device, or caused by the fluid pressures within the drug delivery device and connector.

Basically, adaptors may be secured around the longitudinal tip of the syringe by snap-fitting or friction force, for example by mechanical attaching means defined onto the longitudinal tip such as a groove. However, the incorporation of a groove to the longitudinal tip may cause the longitudinal tip to be sensitive to flaws and may potentially lead to tip breakage. Moreover, an adaptor connected around a longitudinal tip by snap-fitting or friction force may demonstrate both a limited torque and pull out force resistance.

In order to improve the torque and pull out force resistance, it is further known from document WO2016/198580 to provide adaptors with a mounting ring that is shaped and configured such that, when the adaptor is mounted around the longitudinal tip of the drug delivery device, an annular space is created between the mounting ring and the longitudinal tip. The annular space usually accommodates an adhesive layer in order efficiently to bond the adaptor to the longitudinal tip. Such adaptors provide a high torque and pull out force resistance. However, the step of adding an adhesive layer in this annular space entails an increase of the manufacturing costs.

It is also known to provide the longitudinal tip with an outer thread engaging the inner thread of the adaptor. When drug delivery devices are made of plastic, the distance between the outer thread of the longitudinal tip is positioned as close as possible with the distal shoulder of the barrel. This avoids having an undercut, thereby limiting the costs and the complexity of the injection process. Besides, this permits to reduce the length of the longitudinal tip, without reducing the length of its connecting portion between its outer thread and its distal end, thereby limiting the material costs.

SUMMARY OF THE DISCLOSURE

In this context, an object of the present disclosure is to provide a medical container enabling to reduce the manufacturing costs while maintaining a highly reliable connection between this medical container and an element to be attached to said container.

An aspect of the disclosure is a medical container comprising a tubular barrel defining a reservoir for a medical product and a longitudinal distal tip defining a fluid path in communication with said reservoir in order to allow said medical product to be expelled from the medical container, wherein the distal tip and the barrel are made of glass and wherein the distal tip is provided with a thread, said thread being configured to connect said distal tip to a connecting element having a complementarily shaped internal thread. The medical container comprises a distal shoulder connecting the barrel and the distal tip, and the distance d1 between said shoulder and a proximal end of the thread is comprised between 1-5 mm, preferably between 2-4 mm The medical container of the disclosure therefore allows a reliable connection between the distal tip and a connecting element, such as an adaptor, to be connected onto the distal tip. The reliability of the connection relies on the distal tip having an integrated thread. The thread is integrally formed together with the distal tip of the medical container, and is thus being made of glass. Thanks to this thread, the connection of the medical container with the additional element is more reliable than when connected by snap-fitting of friction force.

The reliability of the connection also relies on the distance d1 between the distal shoulder of the barrel and the thread. Having a glass thread distant from the distal shoulder pemits to form the glass thread with a high accuracy, guaranteeing its proper shape, geometry and tolerances. While existing tips are provided with a thread as close as possible to the distal shoulder of the barrel, the disclosure provides, against all expectations, a more reliable connection by putting a glass thread away from this distal shoulder.

Moreover, the assembly of the medical container with an element such as an adaptor only requires the engagement of the thread of the distal tip with an internal thread of said element. Therefore, this assembly does not require any further step such as providing an adhesive layer, so that the connection is less costly than the prior art.

In this application, the connecting element is to be understood as any element that is intended to be mounted onto the distal tip by means of the thread of the distal tip. For example, the connecting element may be a cap or an adaptor, such as a luer lock adaptor, that permits to secure the connection between the distal tip and an additional element.

Preferably, the external major diameter of the distal tip is comprised between 2-12 mm, preferably between 2-6 mm, even more preferably between 3-5 mm.

In this application, the external major diameter of the distal tip is to be understood as the greatest external diameter of said distal tip without including the thread of the distal tip.

Preferably, the medical container comprises a distal end face, and the distance between said distal end face and a distal end of the thread is comprised between 7-9 mm, and is preferably about 8 mm.

Preferably, the distal tip comprises a male connecting portion configured to fit into a complementary female connecting portion of an additional element, and the thread is proximally located relative to this male connecting portion.

In this application, additional element is to be understood as any element that is intended to be connected to the distal tip of the medical container in order to achieve a predetermined function. For example, the additional element may be a needle hub, a cap, or a connector, an IV (Intra Venous), IM (Intra Muscular), or a subcutaneous connector, that may be secured to the distal tip by means of an adaptor, such as a luer lock adaptor.

The distal tip may comprise a cylindrical and/or a frustoconical portion. Preferably, this distal tip comprises a frustoconical portion so as to allow a luer slip or luer lock connection with the additional element. Therefore, the male connecting portion preferably has a frustoconical shape.

In an embodiment, the distal tip comprises a cylindrical portion and the thread is located over said cylindrical portion of the distal tip. Advantageously, when the distal tip also comprises a frustroconical portion, the thread is located over a cylindrical portion of the distal tip, said cylindrical portion being located between the frustroconical portion and the distal shoulder of the medical container.

This offers a greater flexibility of the medical container, permitting said medical container to cooperate with existing adaptors and/or connectors that often have a cylindrical inner thread.

Preferably, the thread of the distal tip is a male external thread.

By male external thread it is meant that the thread of the distal tip outwardly protrudes from an external surface of said distal tip, instead of being formed by inward recesses into said external surface.

Preferably, the pitch thread of the thread is comprised between 0.5-1.5 mm, is preferably about 0.7 mm.

Preferably, the thread axially extends over a total length comprised between 1-5 mm, preferably between 1-4 mm.

Preferably, the thread has a triangular or trapezoid shape, preferably a triangular shape.

Another aspect of the disclosure is a drug delivery device comprising a medical container as above-described and a connecting element that is mounted onto the distal tip of the medical container, said connecting element having a first internal thread engaged with the thread of said distal tip.

Preferably, the connecting element is an adaptor further comprising a second internal thread configured to engage a thread of an additional element that is intended to be fitted onto a connecting portion of the distal tip, said second internal thread having a pitch thread that is greater than that of the thread of the distal tip.

Preferably, the thread of the distal tip is one of a right-handed or left-handed thread, whereas the second internal thread of the adaptor is the other one of a right-handed or left-handed thread.

Alternatively, the thread of the distal tip and the second internal thread of the adaptor are both either right-handed or left-handed threads.

Advantageously, the connecting element is made of a plastic material.

BRIEF DESCRIPTION OF THE DRAWINGS

The Disclosure and the Advantages Arising Therefrom Will Clearly Emerge from the Detailed Description that is Given Below with Reference to the Appended Drawings as Follows.

DETAILED DESCRIPTION

Figure 1:
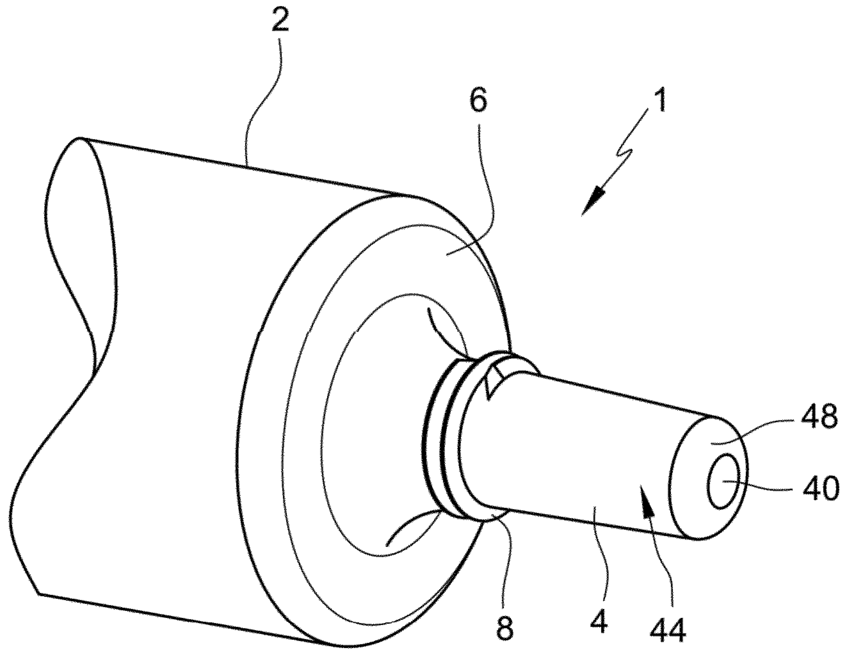
FIG. 1 is a partial perspective view of a medical container according to an embodiment of the disclosure.

With reference to FIG. 1 is shown a medical container 1 according to an embodiment of the disclosure. The medical container 1 comprises a tubular barrel 2 defining a reservoir 20, as shown on FIG. 2, for a medical poduct and a longitudinal distal tip 4 provided at a distal end of the tubular barrel 2. The distal tip 4 defines a fluid path 40 in communication with the reservoir 20 of the tubular barrel 2 in order to allow the medical product to be expelled from the medical container 1. The medical container 1 may comprise a distal shoulder 6 at a distal end of the tubular barrel 2, the distal tip 4 distally protruding from the distal shoulder 6. The tubular barrel 2 and the distal tip 4 are both made out of glass.

The distal tip 4 comprises a thread 8 which is also made out of glass. The thread 8 is configured to connect the distal tip 4 of the medical container 1 to a connecting element, such as an adaptor 10 illustrated on FIG. 2, having a complementarily shaped internal thread 100. The glass distal tip 4 thus has an integrated glass thread 8, thereby allowing a reliable connection between the adaptor 10 and the distal tip 4 of the medical container 1.

The thread 8 may be integrally formed together with the distal tip 4, for example in a single operation. They may also form a single piece with the barrel 2, the barrel 2 being preferably formed first.

The thread 8 is advantageously a male external thread that protrudes from a lateral external surface 42 of the distal tip, rather than being formed by recesses provided inside the external lateral surface 42. This substantially limits risks of breakage of the distal tip 4.

The thread 8 is preferably a helical thread. It may be right-handed or left-handed. Preferably, the thread 8 has a triangular or trapezoid shape, preferably a triangular shape as illustrated on FIGS. 1 and 2.

The distal tip 4 has a major external diameter D that is lower than that of the tubular barrel 2. The external major diameter of the distal tip 4 may be comprised between 2-12 mm, preferably between 2-6 mm, even more preferably between 3-5 mm. For example said external major diameter of the distal tip may be 4.4 mm.

Figure 2:
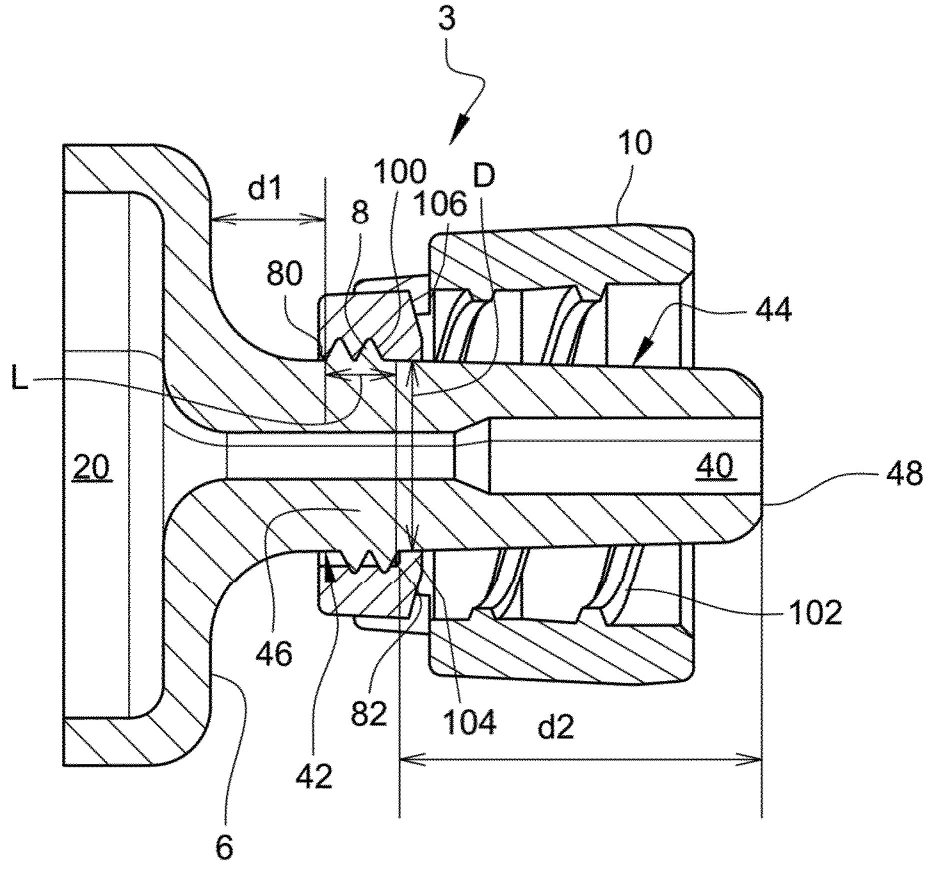
FIG. 2 is a partial cross section view of a medical container according to an embodiment of the disclosure.

As visible on FIGS. 1 and 2, the distal tip 4 comprises a male connecting portion 44 configured to fit into a complementary female connecting portion of an additional element (not shown), such as a connector. The thread 8 may be located on said male connecting portion 44; however, as shown the FIGS. 1 and 2, the thread 8 is preferably proximally located relative to this male connecting portion 44.

The male connecting portion 44 may be cylindrical, or frustoconical as shown on FIGS. 1 and 2 where the distal tip 4 is distally tapered.

Besides, the distal tip 4 may further comprise a cylindrical portion 46 that is arranged proximally relative to the male connecting portion 44, more precisely between the distal shoulder 6 and the male connecting portion 44, the thread 8 being preferably located over said cylindrical portion 46.

The thread 8 of the distal tip 4 is advantageously located closer to the distal shoulder 6 than to a distal end face 48 of the distal tip 4. For example, the distance d1 between said distal shoulder 6 and a proximal end 80 of the thread 8 is comprised between 1-5 mm, preferably between 2-4 mm. Moreover, the distance d2 between said distal end face 48 and a distal end 82 of the thread 8 is advantageously comprised between 7-9 mm, and is preferably about 8 mm. The thread 8 may axially extend over a total length L, which is the distance between its proximal end 80 and its distal end 82, comprised between 1-5 mm, preferably between 1-4 mm.

Preferably, the pitch thread of the thread 8 is comprised between 0.5-1.5 mm, is preferably about 0.7 mm. The pitch thread may have a constant value.

It should also be noted that the height of the thread 8 is comprised between 0.3 and 0.7 mm, and is preferably 0.5 mm. The height of the thread 8 is the distance between the thread crest and the thread root. This height is advantageously constant. As a result, when the thread 8 is located on a cylindrical portion of the distal tip 4, the thread 8 may thus have a constant diameter. When the thread 8 is located on a frustoconical portion of the distal tip 4, the thread 8 may thus have instead a varying diameter, said diameter distally decreasing as the diameter of said frustoconical portion decreases.

The number of revolutions defined by the thread 8 may be comprised between 1-10, preferably 1-5, even more preferably 1-3. For example, the number of revolutions defined by the thread 8 is 2. It should be noted that the number of revolutions defined by the thread 8 is preferably greater than 1 (not equal to).

With reference to FIG. 2, the disclosure also relates to a drug delivery device 3 comprising the medical container 1 as above-described, this medical container 1 thus having the glass distal tip 4 provided with the thread 8, and a connecting element, such as the adpator 10, that is mounted onto the distal tip 4 of the medical container 1, wherein the connecting element has a first internal thread 100 engaged with the thread 8 of the distal tip 4. The medical container 1 may be a syringe and the drug delivery device 3 may be an injection device.

The connecting element, which may be the adaptor 10, is preferably made of a plastic material, more precisely of any rigid polymer adapted to medical use, such as high density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and combinations thereof. Preferably, the adaptor 10 is made of polycarbonate (PC).

As shown on FIG. 2, the adaptor 10 further comprises a second internal thread 102 that is configured to engage a thread of an additional element (not shown) such as a connector, which is intended to be fitted onto the connecting portion 44 of the distal tip 4. The second internal thread 102 may have a pitch thread that is greater than that of the thread 8 of the distal tip 4.

It is contemplated that the thread 8 of the distal tip 4 may be one of a right-handed or left-handed thread, whereas the second internal thread 102 of the adaptor 10 is the other one of a right-handed or left-handed thread. Alternatively, the thread 8 of the distal tip 4 and the second internal thread 102 of the adaptor 10 may be both right-handed or left-handed threads.

With reference to FIG. 2, the adaptor 10 may include a stopper 104 to ensure proper attachment of the adaptor 10. The stopper 104 may be in the form of an inner radial rim defining a proximal shoulder. The thread 8 of the distal tip abuts against the stopper 104 when the adaptor 10 is properly attached. The stopper 104 also prevents the adaptor 10 from abutting against the distal shoulder 6 of the barrel 2. As a result, the proximal end of the adaptor 10 stays remote from the distal shoulder 6.

It is contemplated that the first internal thread 100 and the second internal thread 102 of the adaptor 10 are separated by a distal shoulder 106. The first internal thread 100 is proximal to said distal shoulder 106, while the second internal thread 102 is distal to said distal shoulder 106. As a result, the first and second internal threads 100, 102 of the adaptor 10 are axially offset in a longitudinal direction of the medical container 1. Besides, the second internal thread 102 of the adaptor 10 and the outer surface of the connecting portion 44 directly face each other, without any sleeve of the adaptor extending between them.

The manufacturing method of the medical container 1 may comprise the step of forming the thread 8 and the distal tip 4, and more particularly forming the thread 8 and the connecting portion 44 of the distal tip 4, in a single operation, for example by pressing the distal tip 4 between two forming wheels, such as two rotating forming wheels, said forming wheels being shaped so as to simultaneously form the thread 8 and the distal tip 4 including the connecting portion 44. The forming wheels may have an outer surface provided with recesses configured to form the thread 8. This step may occur after forming the barrel 2.

The invention claimed is:

1. A medical container comprising:

a tubular barrel defining a reservoir for a medical product and a longitudinal distal tip defining a fluid path in communication with the reservoir in order to allow the medical product to be expelled from the medical container; and a connecting element, wherein the distal tip and the barrel are made of glass and wherein the distal tip is provided with a thread, a male connecting portion, and a cylindrical portion proximal to the male connecting portion, the thread being a helical thread and configured to connect the distal tip to a complementarily shaped internal thread of the connecting element, wherein the medical container comprises a distal shoulder connecting the barrel and the distal tip, wherein a distance between the distal shoulder and a proximal end of the thread is between 1-5 mm, wherein the thread is located over the cylindrical portion proximal to the male connecting portion and wherein the distance between the distal shoulder and the proximal end of the thread is smaller than a distance between a distal end face of the distal tip and a distal end of the thread;

wherein the male connecting portion has an external surface, the external surface being a frustoconical shape.

2. The medical container according to claim 1, wherein an external major diameter of the distal tip is between 2-12 mm.

3. The medical container according to claim 1, wherein a distance between the distal end face and the distal end of the thread is between 7-9 mm.

4. The medical container according to claim 1, wherein the male connecting portion is configured to fit into a complementary female connecting portion of an additional element, and the thread is proximally located relative to the male connecting portion.

5. The medical container according to claim 1, wherein the male connecting portion has a frustoconical shape.

6. The medical container according to claim 1, wherein the thread of the distal tip is a male external thread.

7. The medical container according to claim 1, wherein a pitch thread of the thread is between 0.5-1.5 mm.

8. The medical container according to claim 1, wherein the thread axially extends over a total length between 1-5 mm.

9. The medical container according to claim 1, wherein the thread has a triangular or trapezoid shape.

10. The medical container according to claim 1, wherein the distance between the distal shoulder and the proximal end of the thread is between 2-4 mm.

11. The medical container according to claim 1, wherein an external major diameter of the distal tip is between 3-5 mm.

12. The medical container according to claim 1, wherein the distance between the distal end face and the distal end of the thread is about 8 mm.

13. The medical container according to claim 1, wherein a pitch thread of the thread is is about 0.7 mm.

14. The medical container according to claim 1, wherein the thread axially extends over a total length between 1-4 mm.

15. The medical container according to claim 1, wherein the thread has a triangular shape.

16. The medical container according to claim 1, wherein the thread is a single continuous thread.

17. The medical container according to claim 1, wherein the fluid path comprises a proximal section and a distal section, the proximal section having a constant diameter being smaller than a constant diameter of the distal section, the thread being located around the proximal section.

18. A drug delivery device comprising the medical container according to claim 1 and the connecting element that is mounted onto the distal tip of the medical container, the connecting element having a first internal thread, which is the complementarily shaped internal thread, engaged with the thread of the distal tip.

19. The drug delivery device according to claim 18, wherein the connecting element is an adaptor and has a second internal thread configured to engage a thread of an additional element that is intended to be fitted onto the male connecting portion of the distal tip, the second internal thread having a pitch thread greater than that of a pitch thread of the thread of the distal tip.

20. The drug delivery device according to claim 19, wherein the thread of the distal tip is one of a right-handed thread or a left-handed thread, whereas the second internal thread of the adaptor is the other one of the right-handed thread or the left-handed thread.

21. The drug delivery device according to claim 18, wherein the thread of the distal tip and a second internal thread of the connecting element are both either right-handed threads or left-handed threads.

22. The drug delivery device according to claim 18, wherein the connecting element has a second internal thread separated from the first internal thread by a distal shoulder of the connecting element.

* * * * *